United States Patent [19]
Drabek et al.

[11] 3,968,222
[45] July 6, 1976

[54] INSECTICIDAL O,S-DIALKYL ESTERS OF PYRIDYLTHIO-AND-PYRIDYLDITHIO-PHOSPHORIC ACIDS

[75] Inventors: Jozef Drabek; Ernst Beriger, both of Allschwil; Beat Böhner, Binningen, all of Switzerland

[73] Assignee: Ciba-Geigy Corporation, Ardsley, N.Y.

[22] Filed: Jan. 16, 1975

[21] Appl. No.: 541,539

Related U.S. Application Data

[62] Division of Ser. No. 402,647, Oct. 1, 1973, abandoned.

[30] Foreign Application Priority Data

Oct. 13, 1972   Switzerland..................... 15040/72
Aug. 24, 1973   Switzerland..................... 12130/73

[52] U.S. Cl............................ 424/200; 260/294.8 K
[51] Int. Cl.² ............................................ A01N 9/36
[58] Field of Search ............... 424/200; 260/294.8 K

[56] References Cited
UNITED STATES PATENTS

| | | | |
|---|---|---|---|
| 3,669,975 | 6/1972 | Demosay et al. | 260/294.8 K |
| 3,790,582 | 2/1974 | Demosay et al. | 260/294.8 K |
| 3,875,179 | 4/1975 | Dawes et al. | 260/308 R |

*Primary Examiner*—Leonard Schenkman
*Attorney, Agent, or Firm*—Frederick H. Rabin

[57] ABSTRACT

Pyridylthio- or dithiophosphoric acid esters of the formula

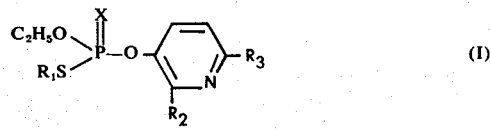

wherein
  $R_1$ represents n-propyl, isobutyl, sec.-butyl or n-pentyl,
  $R_2$ represents hydrogen, chlorine, bromine, cyano, nitro, ($C_1$–$C_4$-alkoxy)carbonyl, mono($C_1$–$C_4$-alkyl)carbamoyl or di($C_1$–$C_4$-alkyl)carbamoyl,
  $R_3$ represents hydrogen, chlorine, bromine or methyl, and
  X represents oxygen or sulphur and their use for combating pests are disclosed.

12 Claims, No Drawings

INSECTICIDAL O,S-DIALKYL ESTERS OF PYRIDYLTHIO-AND-PYRIDYLDITHIO-PHOSPHORIC ACIDS

This is a division of application Ser. No. 402,647, filed on Oct. 1, 1973, now abandoned.

The present invention relates to pyridylthio- and dithiophosphoric acid esters, to processes for their preparation, and to their use in pest control.

The pyridylthio- or dithiophosphoric acid esters correspond to the formula

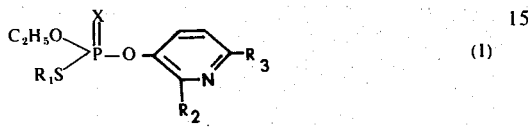

wherein
$R_1$ represents n-propyl, isobutyl, sec.-butyl or n-pentyl,
$R_2$ represents hydrogen, chlorine, bromine, cyano, nitro, ($C_1$–$C_4$-alkoxy)carbonyl, mono($C_1$–$C_4$-alkyl)carbamoyl or di($C_1$–$C_4$-alkyl)carbamoyl,
$R_3$ represents hydrogen, chlorine, bromine or methyl, and
X represents oxygen or sulphur.

The alkyl parts of the mono- or dialkylcarbamoyl groups denoted by $R_2$ and the alkoxy parts of the alkoxycarbonyl groups denoted by $R_2$ can be straight-chain or branched, and can contain 1 to 4 carbon atoms. Examples of such partial groups are: methyl, ethyl, n-propyl, isopropyl, n-butyl and methoxy, ethoxy, n-propoxy, isopropoxy and n-butoxy.

Compounds of formula I which are preferred on account of their action are those wherein
$R_1$ represents n-propyl, n-pentyl, sec.-butyl or isobutyl,
$R_2$ represents hydrogen, chlorine, bromine, cyano, nitro or carbomethoxy,
$R_3$ represents hydrogen, chlorine, bromine or methyl, and
X represents oxygen or sulphur.

To be particularly emphasised are the compounds of formula I wherein
$R_1$ represents n-propyl or sec.-butyl,
$R_2$ represents chlorine or bromine,
$R_3$ represents hydrogen, chlorine, bromine or methyl, and
X represents oxygen or sulphur.

The compounds of formula I can be prepared, for example, by the following methods known per se:

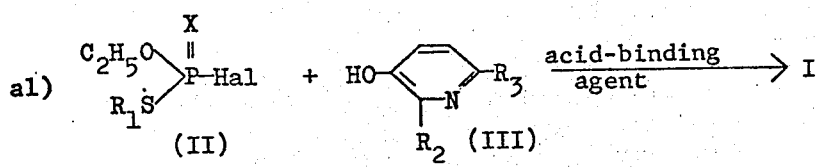

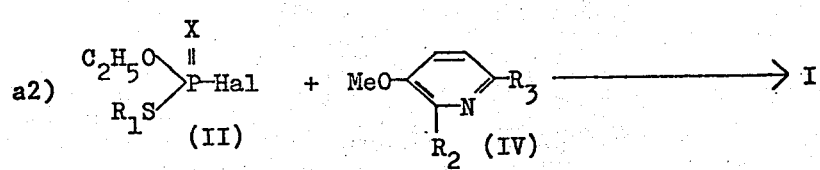

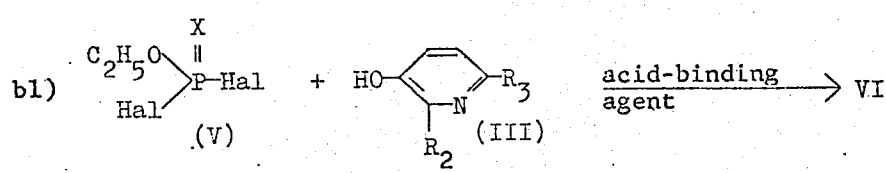

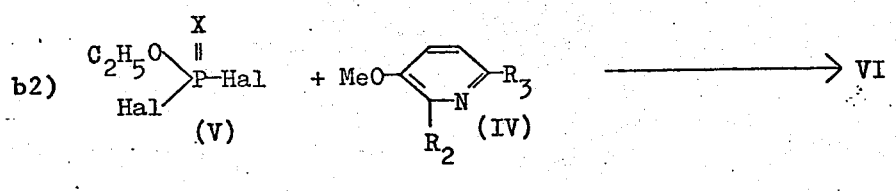

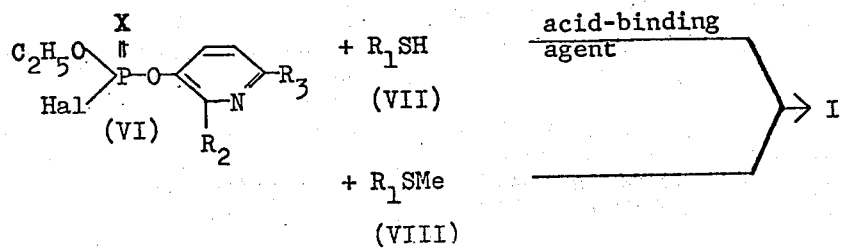

In formulae II to VIII, the symbols $R_1$ to $R_3$ and X have the meanings given for formula I, Hal stands for fluorine, chlorine, bromine or iodine, particularly however for chlorine or bromine, and Me represents a monovalent metal, preferably an alkali metal, especially sodium or potassium.

Suitable acid-binding agents are, for example, the following bases: tertiary amines such as triethylamine, dimethylaniline or pyridine, and inorganic bases such as hydroxides and carbonates of alkali metals and alkaline-earth metals, preferably sodium and potassium carbonate.

The reactions are preferably performed in solvents or diluents that are inert to the reactants. Examples of solvents or diluents suitable for the purpose are as follows: aromatic hydrocarbons such as benzene, toluene or ligroins; halogenated hydrocarbons such as chlorobenzene, polychlorobenzenes or bromobenzene; chlorinated alkanes having 1 to 3 carbon atoms; ethers such as dioxane or tetrahydrofuran; esters such as acetic acid ethyl ester; ketones such as methyl ethyl ketone, diethyl ketone, nitriles, water, etc.

The compounds of formula I have a broad biocidal action, and can be used for the control of diverse plant and animal pests. They are particularly suitable for the control of insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleriidae, Culicidae, Tipulidae, Stomoxydae, Muscidae, Calliphoridae, Trypetidae, Pulicidae; as well as acarids of the families: Ixodidae, Argasidae, Tetranychidae or Dermanyssidae. To be particularly emphasised is their action against Lepidoptera, especially against cotton pests.

The insecticidal or acaricidal action can be substantially broadened and adapted to suit the given conditions by the addition of other insecticides and/or acaricides. Suitable additives include, for examples:
 organic phosphorus compounds,
 nitrophenols and derivatives,
 formamidines,
 ureas,
 carbamates, and
 chlorinated hydrocarbons.

The compounds of formula I are effective also against phytopathogenic nematodes.

The compounds of formula I can be used on their own or together with suitable carriers and/or additives. Suitable carriers and additives may be solid or liquid, and correspond to the substances common in formulation practice, such as, e.g. natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays, or solutions, the formulation of these preparations being effected in a manner commonly known in practice. Also to be mentioned are cattle dips and spray races, in which aqueous preparations are used.

The agents according to the invention are produced in a manner known per se by the intimate mixing and/or grinding of active substances of formula I with the suitable carriers, optionally with the addition of dispersing agents or solvents which are inert to the active substances. The active substances can be obtained and used in the following preparation forms:
 solid preparations: dusts, scattering agents, granulates, coated granulates, impregnated granulates and homogeneous granulates;
 liquid preparations:
  a. water dispersible active substance concentrates: wettable powders, pastes, emulsions;
  b. solutions.

The content of active substance in the described agents is between 0.1 and 95%; it is to be mentioned in this connection that in the case of application from an aeroplane, or by means of other suitable devices, concentrations of up to 99.5% can be employed.

The active substances of formula I can be prepared, for example, as follows:

DUSTS

The following substances are used in the preparation of a) a 5% dust, and b) a 2% dust:
 a. 5 parts of active substance,
  95 parts of talcum;
 b. 2 parts of active substance,
  1 part of highly dispersed silicic acid,
  97 parts of talcum.

The active substances are mixed and ground with the carriers.

GRANULATE

The following substances are used to produce a 5% granulate:
 5 parts of active substance,
 0.25 parts of epichlorhydrin,
 0.25 parts of cetyl polyglycol ether,
 3.50 parts of polyethylene glycol,
 91 parts of kaolin (particle size 0.3 - 0.8 mm).

The active substance is mixed with epichlorhydrin and dissolved with 6 parts of acetone; the polyethylene glycol and cetyl polyglycol ether are then added. The solution thus obtained is sprayed on to kaolin, and the acetone subsequently evaporated off in vacuo.

WETTABLE POWDER

The following constituents are used for the preparation of a) a 40%, b) and c) a 25%, and d) a 10% wettable powder:
 a. 40 parts of active substance,
  5 parts of sodium lignin sulphonate,
  1 part of sodium dibutyl-naphthalene sulphonate,
  54 parts of silicic acid.
 b. 25 parts of active substance,
  4.5 parts of calcium lignin sulphonate
  1.9 parts of Champagne chalk/hydroxyethyl cellulose mixture (1:1),
  1.5 parts of sodium dibutyl naphthalene sulphonate,
  19.5 parts of silicic acid,
  19.5 parts of Champagne chalk,
  28.1 parts of kaolin.
 c. 25 parts of active substance,
  2.5 parts of isooctylphenoxy-polyoxyethyleneethanol
  1.7 parts of Champagne chalk/hydroxyethyl cellulose mixture (1:1),
  8.3 parts of sodium aluminium silicate,
  16.5 parts of kieselguhr,
  46 parts of kaolin.

d. 10 parts of active substance,
  3 parts of a mixture of the sodium salts of saturated fatty alcohol sulphates,
  5 parts of naphthalenesulphonic acid/formaldehyde condensate,
  82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

EMULSIFIABLE CONCENTRATES

The following substances are used to produce (a) a 10% and (b) a 25% emulsifiable concentrate:
  a. 10 parts of active substance,
    3.4 parts of epoxidised vegetable oil,
    13.4 parts of a combination emulsifier consisting of fatty alcohol polyglycol ether and alkylarylsulphonate calcium salt,
    40 parts of dimethylformamide,
    43.2 parts of xylene.
  b. 25 parts of active substance,
    2.5 parts of epoxidised vegetable oil,
    10 parts of an alkylarylsulphonate/fatty alcohol-polyglycol ether mixture
    5 parts of dimethylformamide,
    57.5 parts of xylene.

From these concentrates it is possible to produce, by dilution with water, emulsions of any desired concentration.

SPRAY

The following constituents are used to prepare a 5% spray:
  5 parts of active substance,
  1 part of epichlorhydrin,
  94 parts of ligroin (boiling limits 160°–190°C).

EXAMPLE 1

Preparation of O-ethyl-S-(n)-propyl-O-[3-(2-chloro-4-methyl)-pyridyl)]-thiolphosphate 17.2 g of 2-chloro-6-methyl-3-pyridinol and 12.2 g of triethylamine are dissolved in 150 ml of benzene. An addition is then made dropwise at 10°–15°C, with continuous stirring, of 24.4 g of O-ethyl-S-(n)-propyl-chlorothiophosphate. Stirring is continued for a further 12 hours at room temperature. The reaction mixture is washed with water, and dried over anhydrous sodium sulphate. The benzene is distilled off and the residue maintained for 1 hour at 60°C in high vacuum (0.1 Torr). The resultant product is the compound of the formula

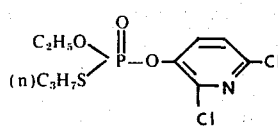

with a refractive index of $n_D^{26} = 1.5255$. Further compounds as listed below are obtained in an analogous manner:

| Structure | Physical data |
|---|---|
| (n)C₃H₇S, C₂H₅O — P(=S) — O — [3-Cl, 6-CH₃ pyridyl] | $n_D^{20} = 1.5703$ |
| (n)C₃H₇S, C₂H₅O — P(=S) — O — [2-Cl pyridyl] | $n_D^{20} = 1.5618$ |
| (n)C₃H₇S, C₂H₅O — P(=S) — O — [2-CN pyridyl] | $n_D^{20} = 1.5575$ |
| (n)C₃H₇S, C₂H₅O — P(=S) — O — [pyridyl] | $n_D^{20} = 1.5492$ |
| (n)C₃H₇S, C₂H₅O — P(=S) — O — [6-CH₃ pyridyl] | $n_D^{20} = 1.5625$ |
| (n)C₃H₇S, C₂H₅O — P(=S) — O — [2,3-diCl pyridyl] | $n_D^{20} = 1.5732$ |
| (n)C₃H₇S, C₂H₅O — P(=S) — O — [2-Br pyridyl] | $n_D^{20} = 1.5764$ |
| (n)C₃H₇S, C₂H₅O — P(=S) — O — [2,6-diBr pyridyl] | $n_D^{20} = 1.5725$ |
| (n)C₃H₇S, C₂H₅O — P(=O) — O — [2-NO₂, 6-CH₃ pyridyl] | $n_D^{20} = 1.519$ |
| (n)C₃H₇S, C₂H₅O — P(=O) — O — [2-NO₂ pyridyl] | $n_D^{20} = 1.523$ |
| (n)C₃H₇S, C₂H₅O — P(=O) — O — [6-CH₃ pyridyl] | $n_D^{20} = 1.5150$ |
| (n)C₃H₇S, C₂H₅O — P(=O) — O — [pyridyl] | $n_D^{20} = 1.5163$ |
| (n)C₅H₁₁S, C₂H₅O — P(=O) — O — [3-Cl, 6-CH₃ pyridyl] | $n_D^{20} = 1.5190$ |
| (n)C₃H₇S, C₂H₅O — P(=S) — O — [2-Cl, 6-Br pyridyl] | $n_D^{20} = 1.5635$ |

-continued

| Structure | Physical data |
|---|---|
| (n)C₃H₇S, C₂H₅O, P=S, —O—pyridine—CONHC₃H₇(i) | $n_D^{20} = 1.5536$ |
| (n)C₃H₇S, C₂H₅O, P=O, —O—pyridine—CONHC₃H₇(i) | $n_D^{20} = 1.5217$ |
| (n)C₃H₇S, C₂H₅O, P=O, —O—pyridine(Br)(Cl) | $n_D^{20} = 1.5234$ |
| (n)C₃H₇S, C₂H₅O, P=S, —O—pyridine—COOCH₃ | |
| (n)C₃H₇S, C₂H₅O, P=S, —O—pyridine(CH₃)(NO₂) | |
| (n)C₃H₇S, C₂H₅O, P=S, —O—pyridine—NO₂ | |
| (n)C₃H₇S, C₂H₅O, P=S, —O—pyridine—COOCH₃ | $n_D^{20} = 1.5573$ |
| (n)C₃H₇S, C₂H₅O, P=S, —O—pyridine—CONHC₃H₇(n) | $n_D^{20} = 1.5528$ |
| (sec.)C₄H₉S, C₂H₅O, P=O, —O—pyridine(CH₃)(Cl) | $n_D^{20} = 1.5174$ |
| (n)C₃H₇S, C₂H₅O, P=O, —O—pyridine—CONHCH₃ | $n_D^{20} = 1.5175$ |
| (sec.)C₄H₉S, C₂H₅O, P=O, —O—pyridine(Cl)(Cl) | |
| (sec.)C₄H₉S, C₂H₅O, P=S, —O—pyridine(CH₃)(Cl) | |
| (sec.)C₄H₉S, C₂H₅O, P=S, —O—pyridine(Cl)(Cl) | |

EXAMPLE 2: INSECTICIDAL ACTION a. Stomach poison action against *Spodoptera littoralis* and *Heliothis virescens*

Tobacco plants were sprayed with a 0.05% aqueous active-substance emulsion (obtained from a 10% emulsifiable concentrate).

After the drying of the coating, *Spodoptera littoralis* caterpillars in the L₃-stage and *Heliothis virescens* caterpillars in the L₃-stage were placed on the tobacco plants. The test was carried out at 24°C with 60% relative humidity.

The compounds according to Example 1 exhibited in the above test a good insecticidal stomach poison action against *Spodoptera littoralis* and *Heliothis virescens*.

b. Contact action against *Aphis fabae*

One day before application of the active-substance emulsion, broad beans (*Vicia faba*) grown in pots were infested with ca. 200 bean aphids (*Aphis fabae*) per plant. The spray emulsion in a concentration of 1000 ppm (prepared from a 25% wettable powder) was applied, by means of a compressed-air sprayer, to the leaves infested with bean aphids. An evaluation was made 24 hours after application. The compounds according to Example 1 exhibited in the above test a good contact action against *Aphis fabae*.

c. Action against *Chilo suppressalis*

Rice plants of the variety Caloro were planted, six plants per pot, in plastic pots having a top diameter of 17 cm, and grown to a height of ca. 60 cm. Infestation with *Chilo suppressalis* larvae (L₁; 3–4 mm long) was carried out 2 days after application of the active substance in granular form (amount applied = 8 kg of active substance per hectare) to the paddy water. An evaluation of the insecticidal action was made 10 days after application of the granules.

The compounds according to Example 1 exhibited in the above test a good action against *Chilo suppressalis*.

d. Persistent action against *Musca domestica*

The active substance formulated as a wettable powder was sprayed, in a concentration corresponding to 1 g of active substance per square meter, onto Petri dishes lines with calcium hydroxide and calcium sulphate coatings. At intervals of 1 day, 8 days and 28 days after the application of the active substance, 4 × 10 polyvalent-resistant and 4 × 10 normal-sensitive house flies (*Musca domestica*) were placed in each case into the dishes. The time up to the point when all the insects were in the dorsal position was recorded.

The compounds according to Example 1 had in the test a good persistent action against normal-sensitive house flies and against resistant house flies.

EXAMPLE 2

Action against ticks

A. *Rhipicephalus bursa*

In two test series, 5 adult ticks or 50 tick larvae were placed into a small glass test tube, and the test tubes then immersed for 1 to 2 minutes in 2 ml. of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

An evaluation in the case of the adults was made after 2 weeks, and in the case of the larvae after 2 days. There were two repeats for each test.

The compounds according to Example 1 exhibited in the above test a good action against adults and larvae of

9

*Rhipicephalus bursa.*

B. *Boophilus microplus* (larvae)

With a dilution series analogous to that in Test A, tests were carried out with, in each case, 20 OP-sensitive larvae.

The compounds according to Example 1 displayed in the above test a good action against sensitive *Boophilus microplus* larvae.

EXAMPLE 3

Action against red spider mites

*Phaseolus vulgaris* (bush beans) were infested, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no running off of the spray liquor. An assessment was made after 2 to 7 days, by examination under a binocular, of the living and of the dead larvae, adults and eggs, and the results expressed in percentages. The treated plants were kept during the "holding time" in greenhouse compartments at 25°C.

The compounds according to Example 1 exhibited a good action in the above test against eggs, larvae and adults of *Tetranychus urticae*.

What we claim is:

1. An insecticidal composition comprising (1) as active ingredient, an insecticidally effective amount of a compound of the formula

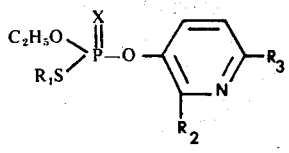

wherein $R_1$ is n-propyl, isobutyl, sec.butyl or n-pentyl, $R_2$ is hydrogen, chlorine, bromine, cyano, nitro, ($C_1$–$C_4$-alkoxy-carbonyl, mono($C_1$–$C_4$-alkyl)-carbamoyl or di($C_1$–$C_4$-alkyl) carbamoyl, $R_3$ represents hydrogen, chlorine, bromine or methyl, and X represents oxygen or sulphur, and (2) a suitable carrier.

2. A method for combatting insects, which comprises applying to said insects an insecticidally effective amount of a compound of the formula

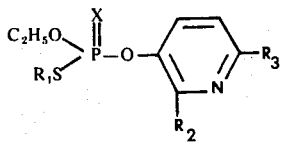

wherein $R_1$ is n-propyl, isobutyl, sec.butyl or n-pentyl, $R_2$ is hydrogen, chlorine, bromine, cyano, nitro($C_1$–$C_4$-alkoxy) carbonyl, mono($C_1$–$C_4$-alkyl)carbamoyl or di($C_1$–$C_4$-alkyl)carbamoyl, $R_3$ represents hydrogen, chlorine, bromine or methyl, and X represents oxygen or sulphur.

3. The method according to claim 2 in which the compound is O-ethyl-S-(n)-propyl-O-[3-(4-methyl)-pyridyl]-dithiophosphate according.

4. The method according to claim 2 in which the compound is O-ethyl-S-(n)-propyl-O-[3-(2-nitro)-pyridyl]-dithiophosphate.

5. The method according to claim 2 in which the compound is O-ethyl-S-(n)-propyl-O-[3-(2-cyano)-pyridyl]-dithiophosphate.

6. A method according to claim 2 in which $R_1$ is n-propyl or sec.butyl and $R_2$ is chlorine or bromine.

7. The method according to claim 6 in which the compound is O-ethyl-S-(n)-propyl-O-[3-(2-chloro-4-methyl)-pyridyl]-thiolphosphate.

8. The method according to claim 6 in which the compound is O-ethyl-S-(n)-propyl-O-[3-(2-chloro-4-methyl)-pyridyl]-dithiophosphate.

9. The method according to claim 6 in which the compound is O-ethyl-S-(n)-propyl-O-[3-(2-chloro)-pyridyl]-dithiophosphate.

10. The method according to claim 6 in which the compound is O-ethyl-S-(n)-propyl-O-[3-(2,4-dichloro)-pyridyl]-dithiophosphate.

11. The method according to claim 6 in which the compound is O-ethyl-S-(sec.)-butyl-O-[3-(2-chloro-4-methyl)-pyridyl]-thiolphosphate.

12. The method according to claim 6 in which the compound is O-ethyl-S-(sec.)-butyl-O-[3-(2,4-dichloro)-pyridyl]-thiolphosphate.

* * * * *